(12) United States Patent
Al-Ali

(10) Patent No.: US 6,950,687 B2
(45) Date of Patent: Sep. 27, 2005

(54) ISOLATION AND COMMUNICATION ELEMENT FOR A RESPOSABLE PULSE OXIMETRY SENSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 257 days.

(21) Appl. No.: 10/351,643

(22) Filed: Jan. 24, 2003

(65) Prior Publication Data

US 2003/0135099 A1 Jul. 17, 2003

Related U.S. Application Data

(63) Continuation-in-part of application No. 10/128,721, filed on Apr. 23, 2002, now Pat. No. 6,725,075, which is a continuation of application No. 09/456,666, filed on Dec. 9, 1999, now Pat. No. 6,377,829.
(60) Provisional application No. 60/351,784, filed on Jan. 25, 2002.

(51) Int. Cl.[7] .................................................. A61B 5/00
(52) U.S. Cl. ........................................ 600/310; 600/344
(58) Field of Search ................................ 600/322–323, 600/310, 344

(56) References Cited

U.S. PATENT DOCUMENTS

| | | | |
|---|---|---|---|
| 4,621,643 A | | 11/1986 | New, Jr. et al. |
| 4,865,038 A | | 9/1989 | Rich et al. |
| 4,974,591 A | * | 12/1990 | Awazu et al. ............... 600/344 |
| 5,090,410 A | | 2/1992 | Saper et al. |
| 5,158,323 A | | 10/1992 | Yamamoto et al. |
| 5,170,786 A | | 12/1992 | Thomas et al. |
| 5,209,230 A | | 5/1993 | Swedlow et al. |
| 5,337,744 A | | 8/1994 | Branigan |
| 5,452,717 A | | 9/1995 | Branigan et al. |
| 5,482,036 A | | 1/1996 | Diab et al. |

(Continued)

FOREIGN PATENT DOCUMENTS

| | | |
|---|---|---|
| EP | 0 313 238 A2 | 10/1988 |
| WO | WO 01/41634 A2 | 6/2001 |

OTHER PUBLICATIONS

PCT International Search Report, App. No.: PCT/US02/22712, App. Date: Jul. 18, 2001, 4 pages.
PCT International Search Report, App. No.: PCT/US00/42637, App. Date: Jul. 12, 2000, 5 pages.
http://www.masimo.com/systemo.htm, "System Overview & Performance", 2 pages, reviewed on Sep. 17, 1999.
http://www.masimo.com/pandt.htm, "Products & Technology", 1 page, reviewed on Sep. 17, 1999.
http://www.masimo.com/cables.htm, "Patient Cables", 1 page, reviewed on Sep. 17, 1999.
http://www.masimo.com/adt.htm, "Inop adt—Adult Disposable Digit Sensor", 1 page, reviewed on Sep. 17, 1999.
http://www.mrequipment.com/products/oximetry patient mntrg.htm, "MR Equipment Magnetic Resonance Equipment Corporation, MR–Compatible High–Performance Optical Fiber Sensors,, Pulse Oximetry Sensors for MRI Fiber Optic Sensors for use with MR–Compatible Pulse Oximeter", 2 pages, reviewed on Sep. 17, 1999.

(Continued)

*Primary Examiner*—Eric F. Winakur
*Assistant Examiner*—Matthew Kremer
(74) *Attorney, Agent, or Firm*—Knobbe, Martens, Olson & Bear LLP

(57) ABSTRACT

A sensor has a connector adapted to electrically communicate with a physiological measurement instrument. A breakable conductor incorporated by the sensor transitions from a continuity state to a discontinuity state as the result of sensor wear. An isolation and communications element (ICE) has an instrument port and an electrically isolated loop port. The instrument port is in communications with the connector and the loop port is in communications with the breakable conductor. The ICE generates a control output responsive to the discontinuity state to render the sensor inoperable.

14 Claims, 16 Drawing Sheets

U.S. PATENT DOCUMENTS

| | | |
|---|---|---|
| 5,490,505 A | 2/1996 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,660,567 A | 8/1997 | Nierlich et al. |
| 5,673,693 A | 10/1997 | Solenberger |
| 5,678,544 A | 10/1997 | DeLonzor et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,779,630 A * | 7/1998 | Fein et al. .................. 600/323 |
| 5,782,757 A | 7/1998 | Diab et al. |
| 5,823,950 A | 10/1998 | Diab et al. |
| 5,860,919 A | 1/1999 | Kiani-Azarbayjany et al. |
| 5,890,929 A | 4/1999 | Mills et al. |
| 5,919,133 A | 7/1999 | Taylor et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A * | 11/1999 | Kiani et al. ................. 600/310 |
| 5,997,343 A | 12/1999 | Mills et al. |
| 5,999,834 A | 12/1999 | Wang et al. |
| 6,002,952 A | 12/1999 | Diab et al. |
| 6,011,986 A | 1/2000 | Diab et al. |
| 6,014,576 A | 1/2000 | Raley |
| 6,036,642 A | 3/2000 | Diab et al. |
| 6,061,584 A | 5/2000 | Lovejoy et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,308,089 B1 | 10/2001 | von der Ruhr et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,571,113 B1 * | 5/2003 | Fein et al. .................. 600/323 |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |

OTHER PUBLICATIONS

Masimo Corporation, "Discrete Saturation Transform Example", reviewed on Sep. 17, 1999.

MSP Industry Alert, "Masimo To Introduce NR7 At ASA", pp. 18, 19, and the front and back cover, vol. 3, No. 3, Fall 2001.

* cited by examiner

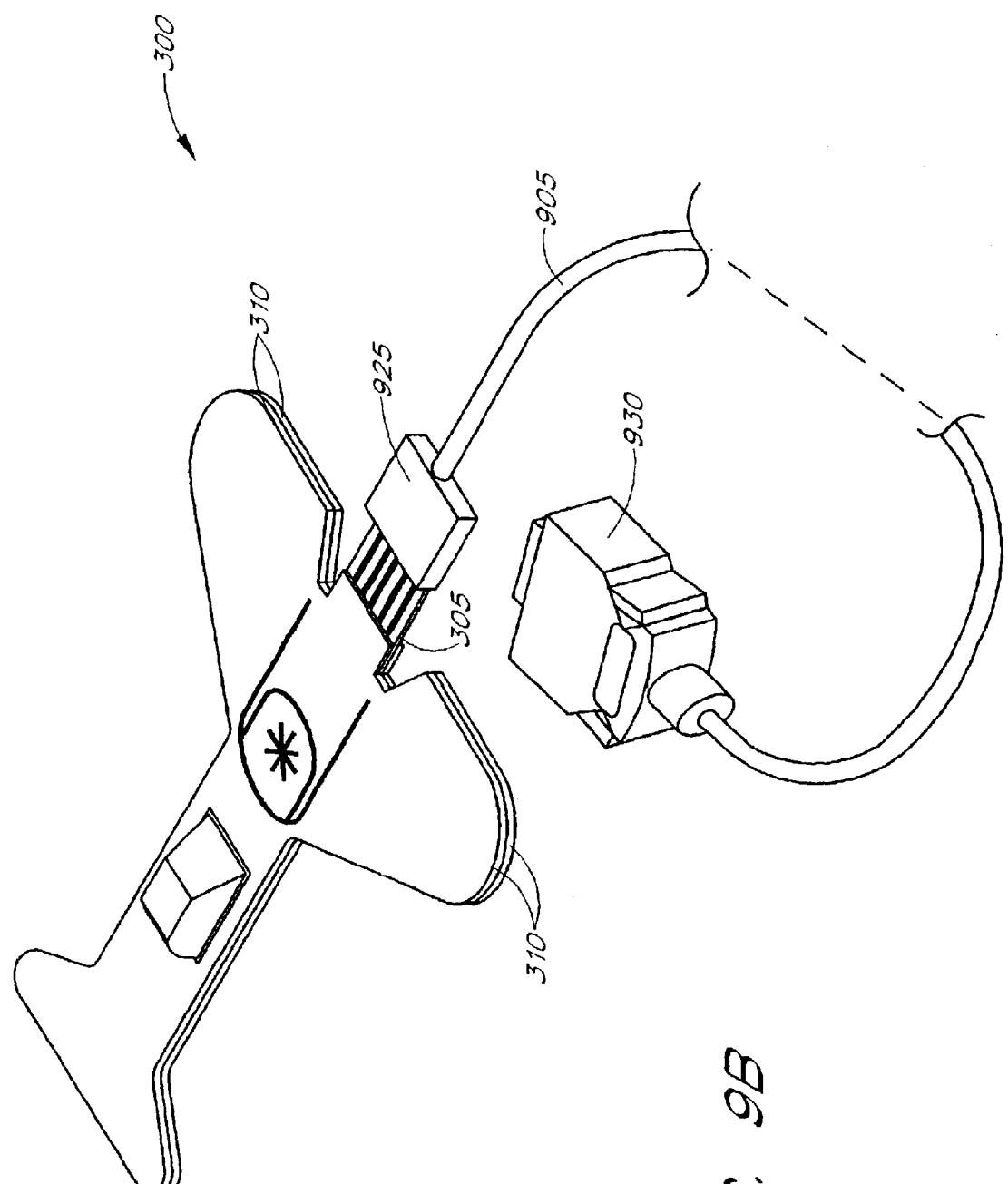

ISOLATION AND COMMUNICATION ELEMENT FOR A RESPOSABLE PULSE OXIMETRY SENSOR

CROSS-REFERENCE TO RELATED APPLICATIONS

The present application claims priority benefit under 35 U.S.C. § 120 to and is a continuation-in-part of U.S. patent application Ser. No. 10/128,721, filed Apr. 23, 2002, now U.S. Pat. No. 6,725,075 entitled "Resposable Pulse Oximetry Sensor," which is a continuation of U.S. patent application Ser. No. 09/456,666 filed Dec. 9, 1999, now U.S. Pat. No. 6,377,829, entitled "Resposable Pulse Oximetry Sensor." Moreover, the present application claims priority benefit under 35 U.S.C. § 119(e) to U.S. Provisional Patent Application Ser. No. 60/351,784, filed Jan. 25, 2002, entitled "Isolation and Communication Element for a Resposable Pulse Oximetry Sensor." The present application incorporates the foregoing disclosures herein by reference.

BACKGROUND OF THE INVENTION

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed oximetry, a study and measurement of the oxygen status of blood. One particular type of oximetry, pulse oximetry, is a widely accepted noninvasive procedure for measuring the oxygen saturation level of arterial blood, an indicator of the oxygen status of the blood. A pulse oximeter relies on a sensor attached to a patient in order to measure the blood oxygen saturation.

Conventionally, a pulse oximeter sensor has a red emitter, an infrared emitter, and a photodiode detector. The sensor is typically attached to a patient's finger, earlobe, or foot. For a finger, the sensor is configured so that the emitters project light through the outer tissue of the finger and into the blood vessels and capillaries contained inside. The photodiode is positioned at the opposite side of the finger to detect the emitted light as it emerges from the outer tissues of the finger. The photodiode generates a signal based on the emitted light and relays that signal to a pulse oximeter. The pulse oximeter determines blood oxygen saturation by computing the differential absorption by the arterial blood of the two wavelengths (red and infrared) emitted by the sensor.

Conventional sensors are either disposable or reusable. A disposable sensor is typically attached to the patient with an adhesive wrap, providing a secure contact between the patient's skin and the sensor components. A reusable sensor is typically a clip that is easily attached and removed, or reusable circuitry that employs a disposable attachment mechanism, such as an adhesive tape or bandage.

The disposable sensor has the advantage of superior performance due to conformance of the sensor to the skin and the rejection of ambient light. However, repeated removal and reattachment of the adhesive tape results in deterioration of the adhesive properties and tearing of the tape. Further, the tape eventually becomes soiled and is a potential source of cross-patient contamination. The disposable sensor must then be thrown away, wasting the long-lived emitters, photodiode and related circuitry.

On the other hand, the clip-type reusable sensor has the advantage of superior cost savings in that the reusable pulse sensor does not waste the long-lived and expensive sensor circuitry. However, as mentioned above, the clip-type reusable sensor does not conform as easily to differing patient skin shape, resulting in diminished sensitivity and increased ambient light.

Similar to the clip-type reusable sensor, the circuit-type reusable sensor advantageously does not waste the sensor circuitry. On the other hand, the circuit-type reusable sensor fails to provide quality control over the attachment mechanism. Much like the disposable sensors, the attachment mechanism for the circuit-type reusable sensor may become soiled or damaged, thereby leading to cross-patient contamination or improper attachment. Moreover, because the reusable circuit is severable from the attachment mechanism, operators are free to use attachment mechanisms that are either unsafe or improper with regard to a particular type of reusable circuitry.

Based on the foregoing, significant and costly drawbacks exist in conventional disposable and reusable oximetry sensors. Thus, a need exists for a pulse oximetry sensor that incorporates the advantages found in the disposable and reusable sensors, without the respective disadvantages.

SUMMARY OF THE INVENTION

A reusable sensor with the performance features of a disposable may incorporate a disposable adhesive tape component that can be removed from other reusable sensor components. The disposable tape may include a mechanism for the electrical connection of an information element to the emitters, where the information element provides an indication to an attached pulse oximeter of various aspects of the sensor and also insures the sensor is from an authorized supplier. The information element electrical connection mechanism may be a breakable conductor located within the disposable component such that excessive wear of the disposable component prevents connection of the information element to an attached pulse oximeter, thereby indicating that the disposable component should be replaced. There are some drawbacks to this approach, however, including patient-instrument electrical isolation and electromagnetic interference (EMI).

Electrical isolation between an electrical source and a patient needs to be 4,000V. A pulse oximeter instrument typically provides 2,500V of isolation and a pulse oximeter sensor another 1,500V. The 1,500V sensor isolation is difficult to achieve with a breakable conductor located within the tape used for patient sensor attachment. Further, a breakable conductor formed as a loop around the periphery of the disposable attachment tape, although advantageous for wear detection, creates an antenna that receives EMI, which can be conducted directly into the sensor circuitry.

A sensor incorporating an isolation and communications element (ICE) that reduces or eliminates the aforementioned drawbacks has a connector adapted to electrically communicate with a physiological measurement instrument, such as a pulse oximeter. A breakable conductor incorporated by the sensor transitions from a continuity state to a discontinuity state as the result of sensor wear. An isolation and communications element (ICE) has an instrument port and an electrically isolated loop port. The instrument port is in communications with the connector and the loop port is in communications with the breakable conductor. The ICE generates a control output responsive to the discontinuity state to render the sensor inoperable.

BRIEF DESCRIPTION OF THE DRAWINGS

FIG. 9B illustrates a perspective view of a resposable sensor having a reusable portion removably attached to a patient cable, according to another embodiment of the invention.

DETAILED DESCRIPTION OF THE PREFERRED EMBODIMENT

Resposable Pulse Oximeter Sensor

The configuration of an information element for an oximeter sensor and method of reading an information element with an attached oximeter is described in U.S. Pat. No. 5,758,644 entitled "Manual And Automatic Probe Calibration," assigned to Masimo Corporation, Irvine, Calif. and incorporated by reference herein. Accordingly, the configuration and the implementation of an information element will be greatly summarized as follows.

Figure 1:
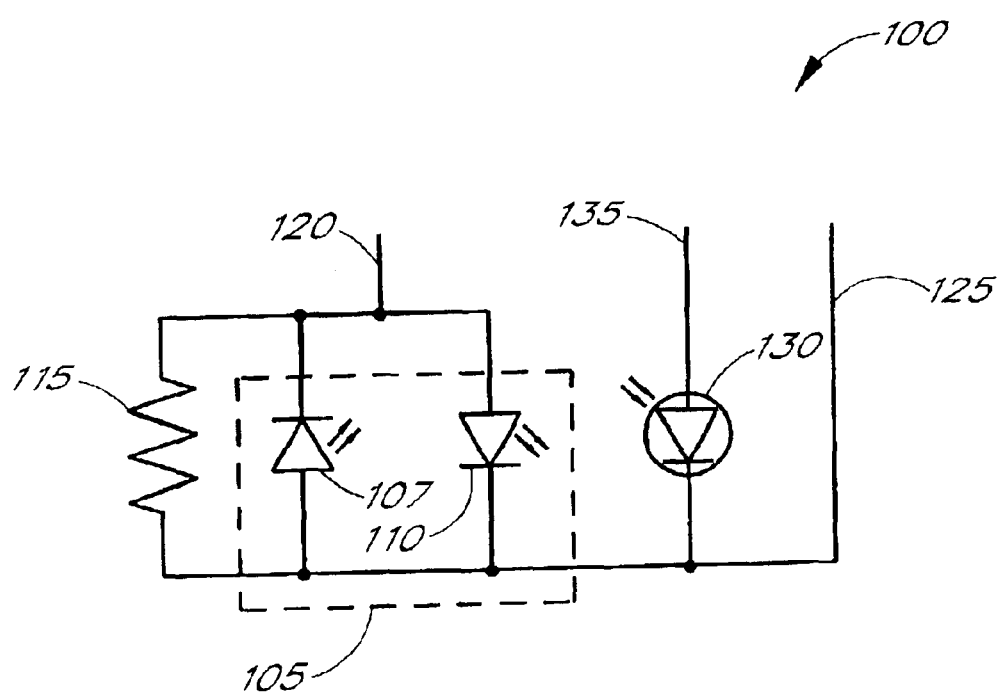
FIG. 1 illustrates a circuit diagram of a conventional disposable sensor having an information element.

FIG. 1 illustrates a conventional oximeter sensor circuit 100. The oximeter sensor circuit 100 includes an emitter 105 comprising a first LED 107 and a second LED 110. The oximeter sensor circuit further includes an information element comprising a resistor 115. The first LED 107, the second LED 110 and the resistor 115 are connected in parallel. The parallel connection has a common input electrical connection 120 and a common return 125. The oximeter sensor circuit 100 also includes a photodetector 130 having an input electrical connection 135 connected to one end and having the common return 125 connected to the other end.

As mentioned, the resistor 115 is provided as an information element that can be read by an attached oximeter. In order to read the resistor 115, the oximeter drives the oximeter sensor circuit 100 at a level where the emitter 105 draws effectively insignificant current. As is well understood in the art, the emitter 105 becomes active only if driven at a voltage above a threshold level. Thus, at this low level, significantly all of the current through the input electrical connection 120 flows through the resistor 115. By reducing the drive voltage across the input electrical connection 120 and common return 125 to a low enough level to not activate the emitter 105, the emitter 105 is effectively removed from the oximeter sensor circuit 100. Thus, the oximeter can determine the value of the resistor 115.

The value of the resistor 115 can be preselected to indicate, for example, the type of sensor (e.g., adult, pediatric, or neonatal), the operating wavelength, or other parameters about the sensor. The resistor 115 may also be utilized for security and quality control purposes. For example, the resistor 115 may be used to ensure that the oximeter sensor circuit 100 is configured properly for a given oximeter. For instance, the resistor 115 may be utilized to indicate that the oximeter sensor circuit 100 is from an authorized supplier.

An information element other than the resistor 115 may also be utilized. The information element need not be a passive device. Coding information may also be provided through an active circuit, such as a transistor network, memory chip, or other identification device.

Furthermore, it will be understood by a skilled artisan that a number of different circuit configurations can be implemented that allow the oximeter sensor circuit 100 to include an information element. For example, the emitter 105 and the information element may each have individual electrical connections.

As mentioned above, the resistor 115 is preselected such that at low drive voltages, it is the only circuit element sensed by the oximeter. On the other hand, the resistor 115 can also be preselected be of a sufficiently high value that when the drive voltage rises to a level sufficient to drive the emitter 105, the resistor 115 is effectively removed from the oximeter sensor circuit 100. Thus, the resistor 115 does not affect normal operations of the emitter 105. In summary, an information element may form an integral part of the oximeter sensor circuit 100 by providing valuable information to the attached oximeter.

Figure 2A:
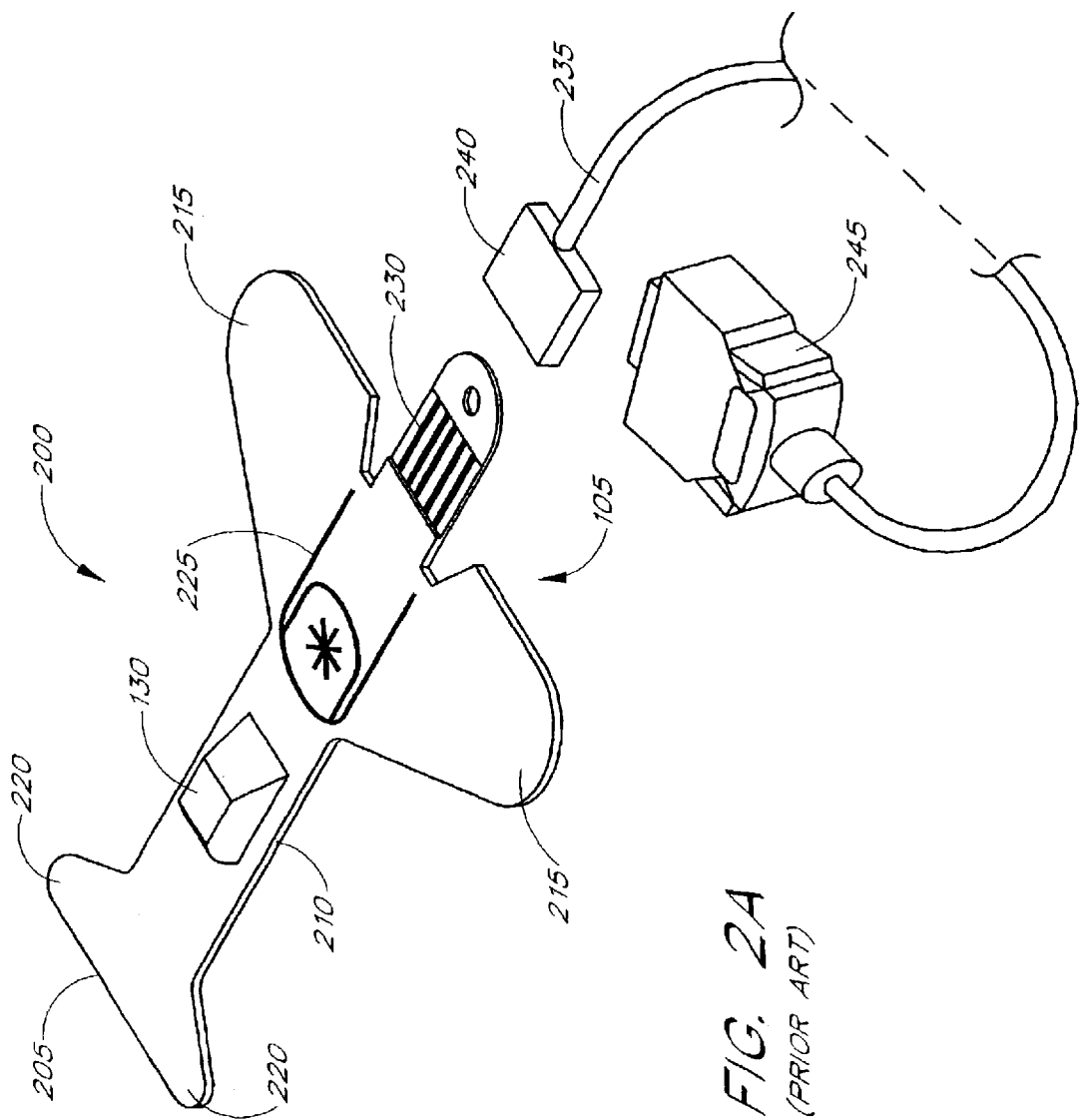
FIGS. 2A and 2B illustrate perspective views of the conventional disposable sensor.
Figure 2B:
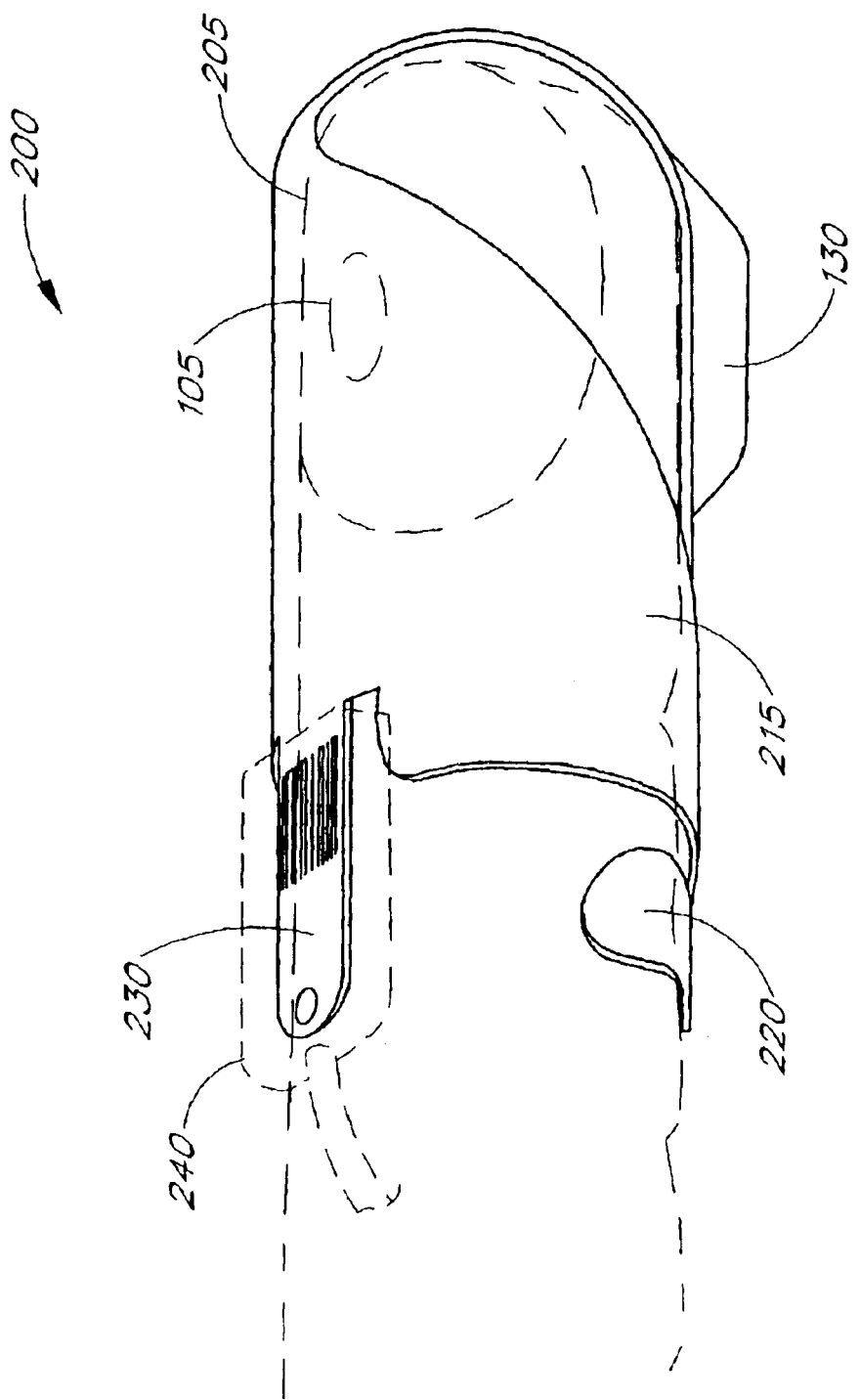

FIGS. 2A and 2B illustrate a conventional disposable sensor 200. The disposable sensor 200 includes an adhesive substrate 205 having an elongated center portion 210 with front and rear flaps, 215 and 220, extending outward from the elongated center portion 210. The adhesive substrate 205 may also have an image 225 superimposed on the adhesive substrate 205 so as to indicate proper use.

The elongated center portion 210 includes the oximeter sensor circuit 100 of FIG. 1. For example, the emitter 105 is housed on an underside of the elongated center portion 210 approximately beneath the superimposed image 225. Thus, as shown in FIG. 2A, the emitter 105 may be housed approximately beneath the asterisk superimposed on the image of a fingernail. On the other hand, the photodetector 130 is housed on the topside of the elongated center portion 210 in proximity with the rear flaps 220.

The elongated center portion 210 further includes an electrical connector 230 to drive the emitter 105 and to receive an output from the photodetector 130. The electrical connector 230 is preferably configured to attach to a connector cable 235 via a sensor connector 240. Also, the connector cable 235 attaches to or connects with an oximeter via an oximeter connector 245.

FIG. 2B illustrates an example of how the disposable sensor 200 wraps the front and rear flaps 215 and 220 around a finger such that the adhesive substrate 205 provides a secure contact between the patient's skin, the emitter 105 and the photodetector 130. FIG. 2B also illustrates an example of the sensor connector 240 (shown in broken lines) encompassing the electrical connector 230.

As shown in FIGS. 1–2B, the conventional disposable sensor 200 integrates the components of the conventional oximeter sensor circuit 100 such that disposal of the disposable sensor 200 includes disposal of the longer lasting, expensive circuitry found therein.

Figure 3:
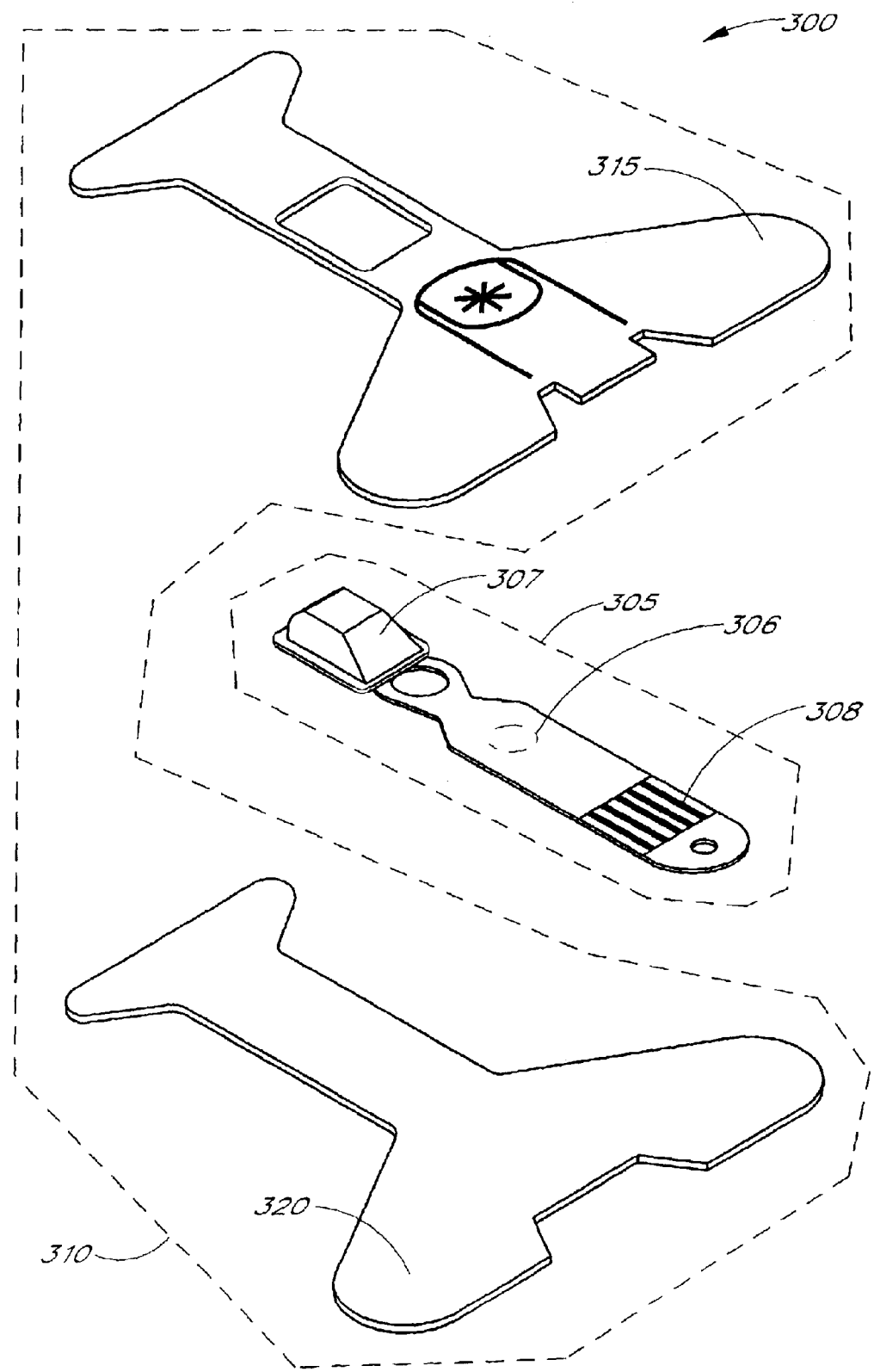
FIG. 3 illustrates an exploded view of a resposable sensor having two disposable tape layers, according to one embodiment of the invention.

FIG. 3 illustrates an exploded view of one embodiment of a resposable (reusable/disposable) sensor 300. In this embodiment, the resposable sensor 300 includes a reusable portion 305 having an emitter 306, a photodetector 307 and an electrical connector 308. The resposable sensor also includes a disposable portion 310 having a face tape layer 315 and a clear base tape layer 320. As shown in FIG. 3, the disposable portion 310 attaches to the reusable portion 305 by sandwiching the reusable portion 305 between a face tape layer 315 and a clear base tape layer 320.

According to this embodiment, conventional adhesives or other attaching methodology may be used to removably attach the face tape layer 315 to the clear base tape layer 320. Furthermore, the adhesive properties associated with the base of the conventional disposable sensor 200 may be the same as the adhesive properties on the base of the clear base tape layer 320, as both portions are provided to attach to the patient's skin.

As mentioned, the disposable portion 310 removably attaches to the reusable portion 305 in, for example, a sandwich or layered style. After removably attaching the disposable portion 310 to the reusable portion 305, the resposable sensor 300 functions similar to the disposable sensor 200, i.e., the resposable sensor 300 wraps flaps around a patient's tissue such that the emitter 306 and the photodetector 307 align on opposite sides of the tissue. However, in contrast to the disposable sensor 200, the resposable sensor 300 provides for reuse of the reusable portion 305. For example, when the disposable portion 310 becomes contaminated, worn, or defective, rather than discarding the entire resposable sensor 300, the disposable portion 310 is removed such that the reusable portion 305 may be re-removably attached to a new disposable portion 310. The discarding of the disposable portion 310 completely avoids cross-contamination through the reuse of adhesive tapes between patients without wasting the more costly and longer lasting sensor circuitry of the resposable portion 305. Note that optional sterilization procedures may be advantageously performed on the reusable portion 305 before reattachment to either the new disposable portion 310 or to the patient, in order to further ensure patient safety.

Figure 4:
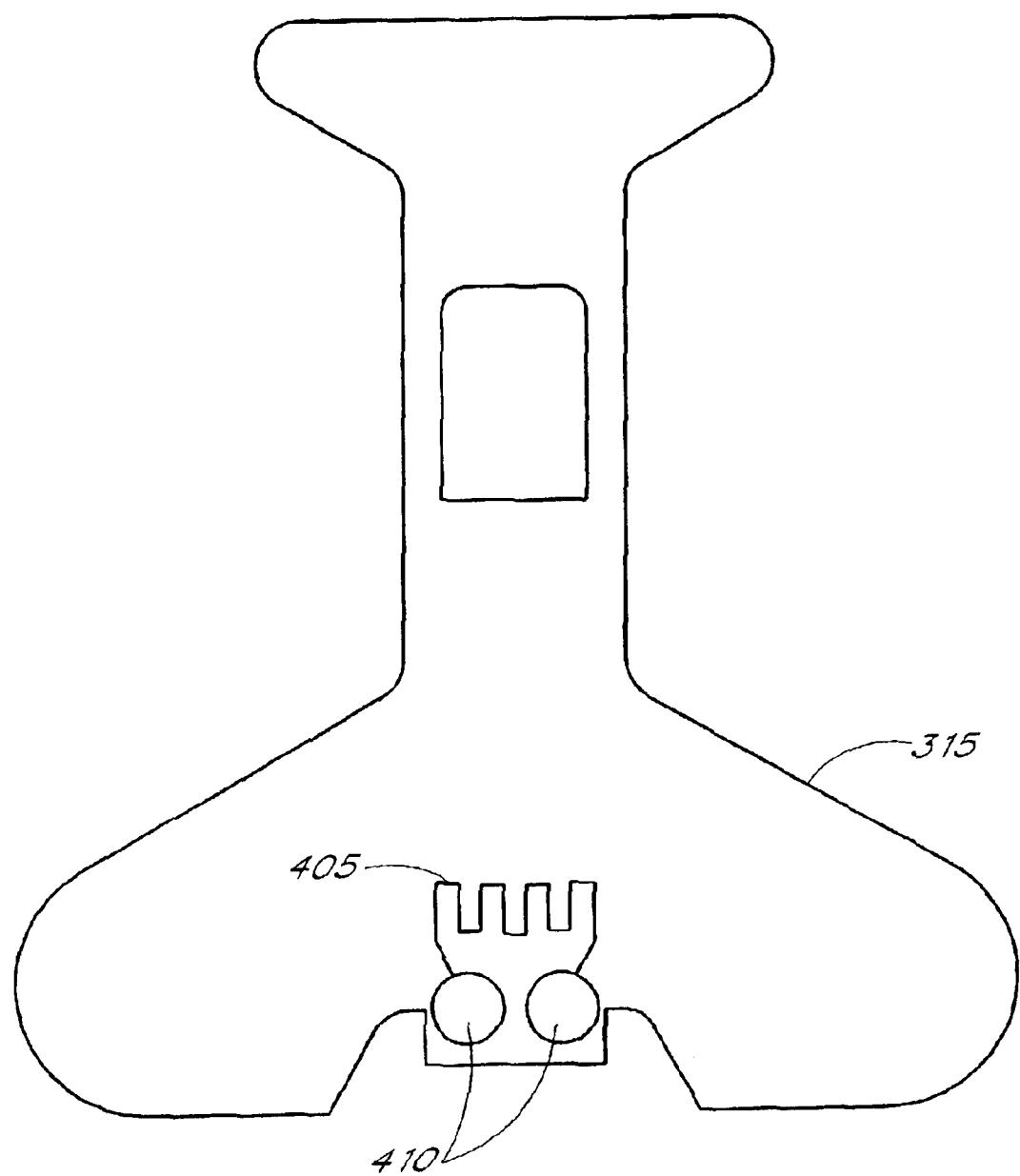
FIG. 4 illustrates a top view of one of the disposable tape layers of FIG. 3 incorporating an information element.

FIG. 4 illustrates a top view of an embodiment of the face tape layer 315 of the disposable portion 310 of the resposable sensor 300. According to this embodiment, the face tape layer 315 further includes an information element 405 as an integral part of the face tape layer 315. In this embodiment, the information element 405 is a resistive element made by depositing a conductive ink trace having a predetermined length and width. As is known in the art, the length, width and conductivity of the conductive ink trace determines the resistance of the resistive element. The information element 405 is deposited between contacts 410 that are also implemented with conductive ink. It will be understood by a skilled artisan that a variety of methods can be used for mating the contacts 410 with the electrical circuitry of the reusable portion 305. For example, the contacts 410 may advantageously physically touch the leads or the electrical connector 308 such that the reusable portion 305 is electrically configured to include the information element 405. Such a configuration employs the oximeter sensor circuit 100 of FIG. 1, having elements thereof distributed in both the reusable portion 305 and the disposable portion 310 of the resposable sensor 300.

In the foregoing embodiment, the disposable portion 310 comprises the information element 405 along with the face tape layer 315 and the clear base layer 320. As mentioned, the disposable portion 310 is removably attached to the reusable portion 305 and is employed in a similar manner as the disposable sensor 200. In contrast to the disposable sensor 200, when the disposable portion 310 of the resposable sensor 300 becomes worn, the disposable portion 310 and the information element 405 are discarded and the reusable portion 305 is saved. By discarding the information element, the attached oximeter can perform quality control. For example, if the reusable portion 305 is reattached to a patient using either a simple adhesive or any other non-authorized disposable mechanism, the resposable sensor 300 will not include the information element 405. As mentioned above, an attached oximeter can recognize the absence of the information element 405 and create an appropriate response indicating inappropriate use of the reusable portion 305 of the resposable sensor 300.

Figure 5:
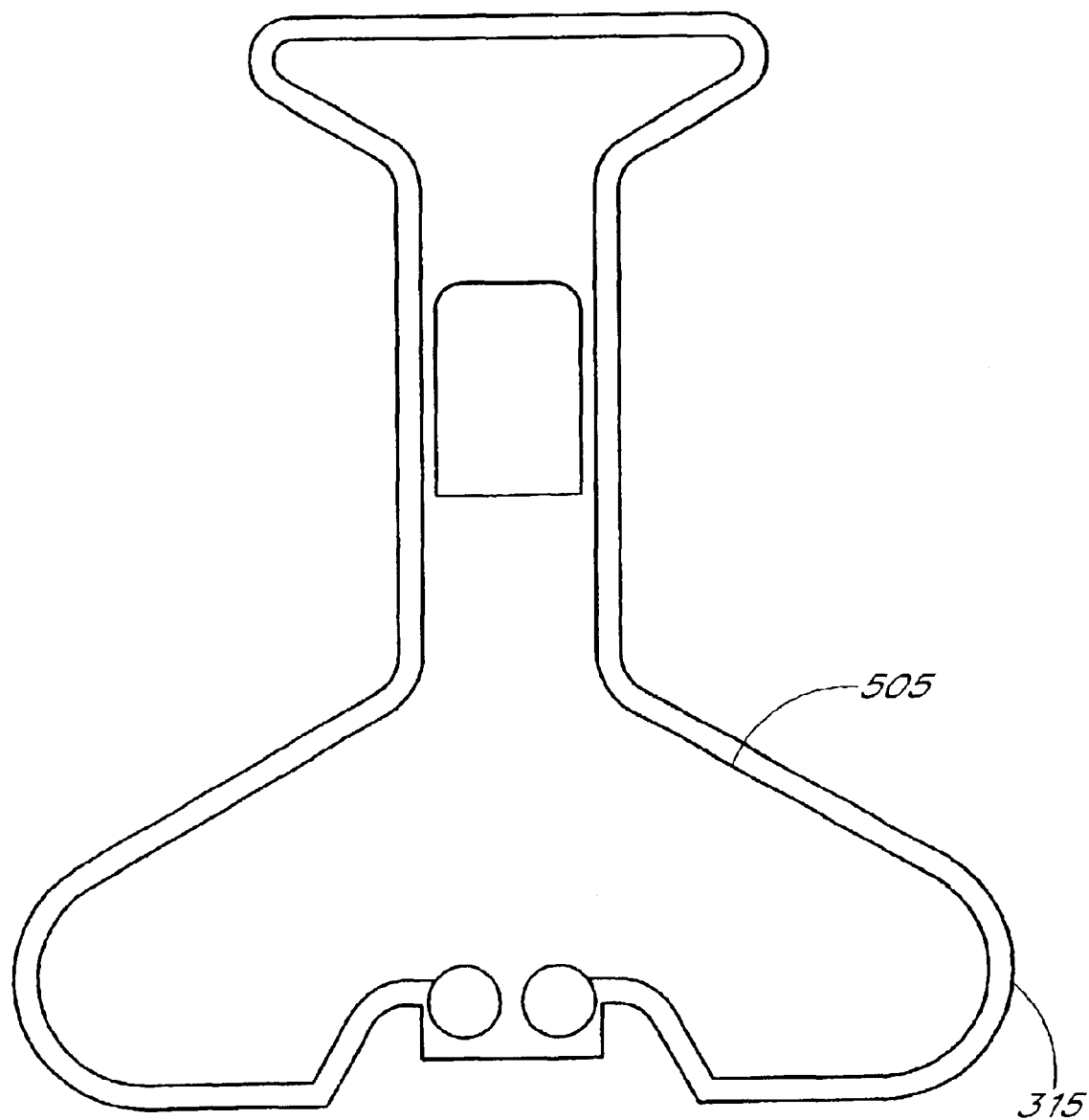
FIG. 5 illustrates a top view of one of the disposable tape layers of FIG. 3 incorporating a breakable conductor.
Figure 6A:
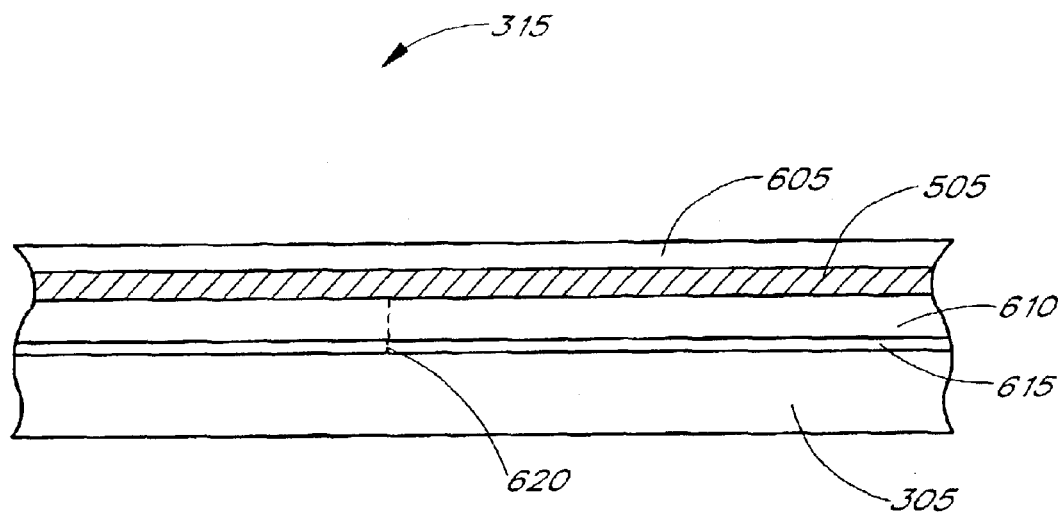
FIGS. 6A and 6B illustrate cross-sectional views of a portion of the disposable tape layer of FIG. 5.
Figure 6B:
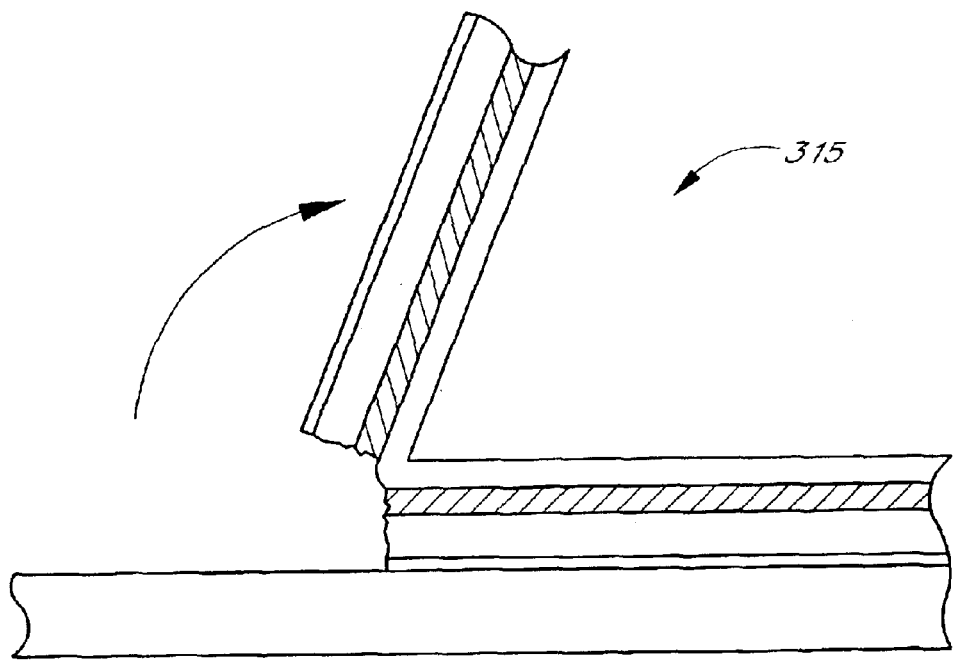

FIG. 5 illustrates a top view of yet another embodiment of the face tape layer 315 of the disposable portion 310 of the resposable sensor 300. In this embodiment, the face tape layer 315 includes a breakable conductor 505 comprising a conductive ink trace located approximately along the periphery of the face tape layer 315. This location ensures that a tear along the periphery of the face tape layer 315 results in a tear, or electrical discontinuity, in the breakable conductor 505. For example, FIGS. 6A and 6B illustrate the face tape layer 315 in which the breakable conductor 505 is layered between a tape stock 605 and a tape base 610. The reusable portion 305 of the resposable sensor 300 then attaches to the tape base 610 through a pressure sensitive adhesive (PSA) 615. The PSA 615, the conductor 505 and the tape base 610 include a score 620 such that multiple attachment and removal of the resposable sensor 300 will result in a peripheral tear, or electrical discontinuity, in the breakable conductor 505, as illustrated in FIG. 6B.

Thus, like the information element 405, the breakable conductor 505 also provides security and quality control functions. In particular, repeated use of the disposable portion 305 of the resposable sensor 300 advantageously severs at least one part of the breakable conductor 505. An attached oximeter can detect such severance and initiate an appropriate notification to, for example, monitoring medical personnel. Providing security and quality control through a breakable conductor advantageously assists in controlling problems with patient contamination or improper attachment due to weakened adhesives.

Figure 7:
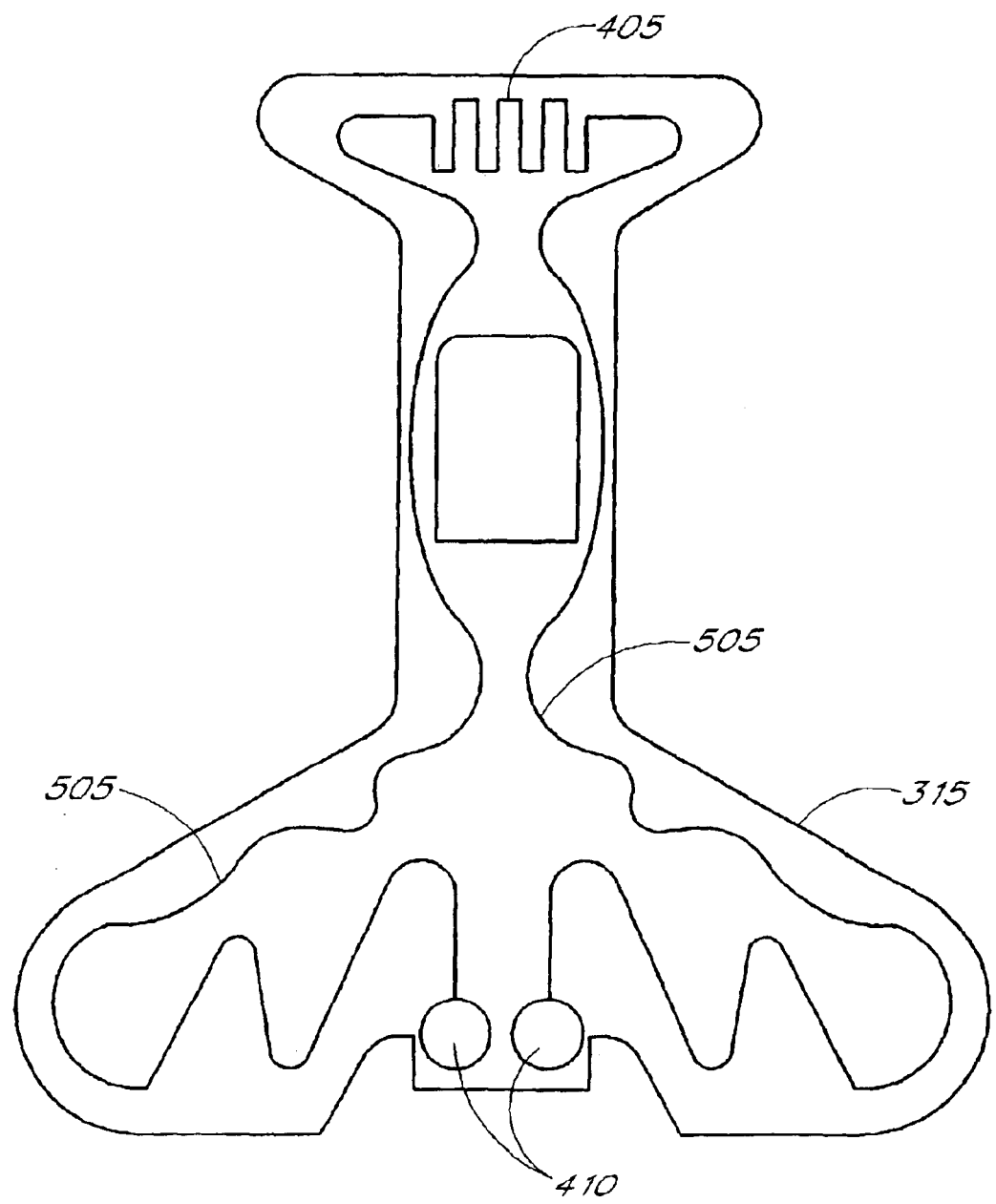
FIG. 7 illustrates a top view of one of the disposable tape layers of FIG. 3 incorporating the information element with a breakable conductor.

FIG. 7 illustrates yet another embodiment of the face tape layer 315. In this embodiment, the face tape layer 315 combines the breakable conductor 505 and the information element 405. In this embodiment, the breakable conductor 505 is printed in a serpentine pattern to further increase the probability of a discontinuity upon the tearing of any portion of the face tape layer 315. This combination of the information element 405 and the breakable conductor 505 advantageously adds significant safety features. For example, in this embodiment, the information element 405 is connected serially with the breakable conductor 505 and in parallel with the emitter 306 of the reusable portion 305. Therefore, any discontinuity or tear in the breakable conductor 505 separates the information element 405 from the circuitry of the reusable portion 305.

According to the foregoing embodiment, the attached oximeter receives an indication of both overuse and misuse of the resposable sensor 300. For example, overuse is detected through the tearing and breaking of the breakable conductor 505, thereby removing the information element 405 from the resposable sensor 300 circuitry. In addition, misuse through employment of disposable portions 310 from unauthorized vendors is detected through the absence of the information element 405. Moreover, misuse from purposeful shorting of the contacts 410 is detected by effectively removing the emitter 306 from the circuit, thereby rendering the resposable sensor 300 inoperative. Therefore, the resposable sensor 300 of this embodiment advantageously provides a multitude of problem indicators to the attached oximeter. By doing so, the resposable sensor 300 advantageously prevents the likelihood of contamination, adhesive failure, and misuse. The resposable sensor 300 also advantageously maintains the likelihood of quality control.

A skilled artisan will recognize that the concepts of FIGS. 3–7 may be combined in total or in part in a wide variety of devices. For example, either or both of the breakable conductor 505 and the information element 405 may advantageously be traced into the clear base tape layer 320 rather than into the face tape layer 315.

Figure 8A:
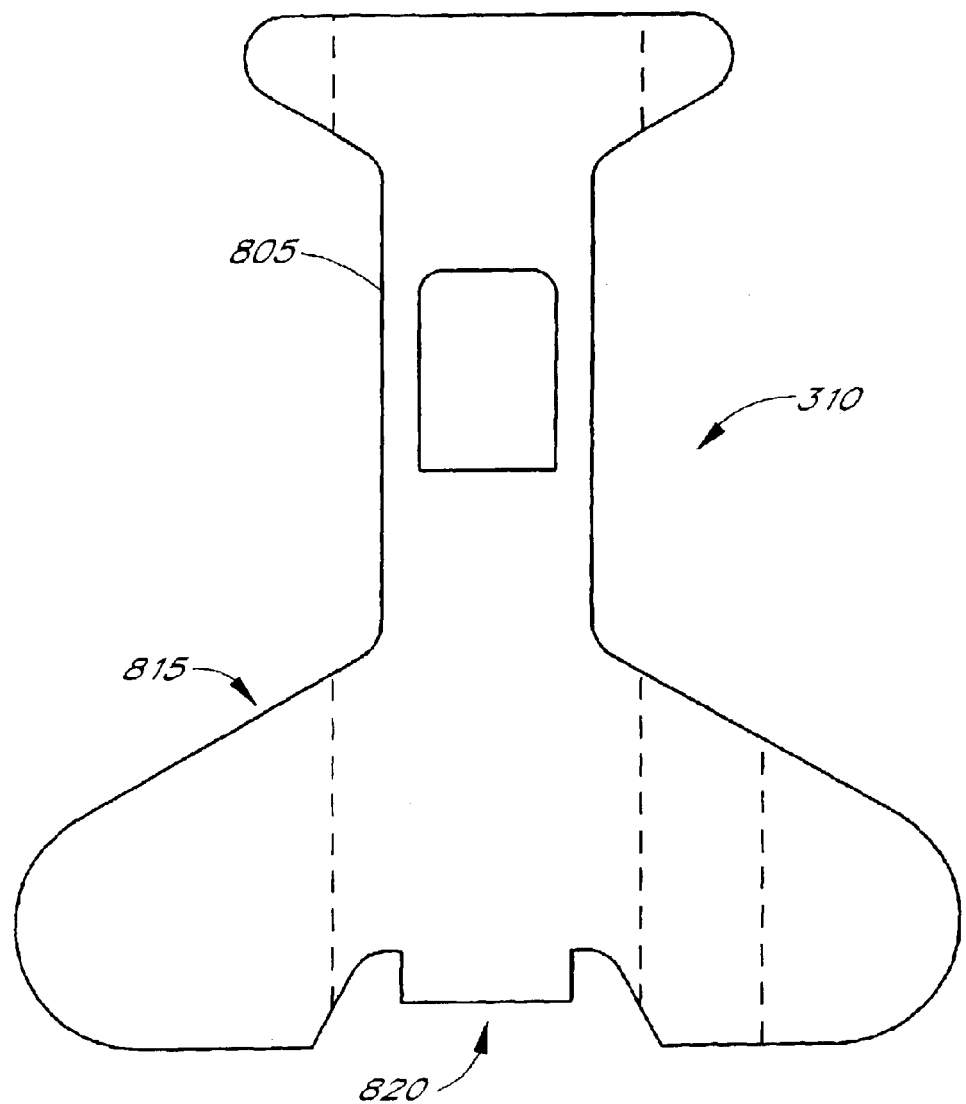
FIGS. 8A and 8B illustrate a top view and a side view, respectively, of one of the disposable layers of FIG. 3 configured as a fold-over tape.
Figure 8B:
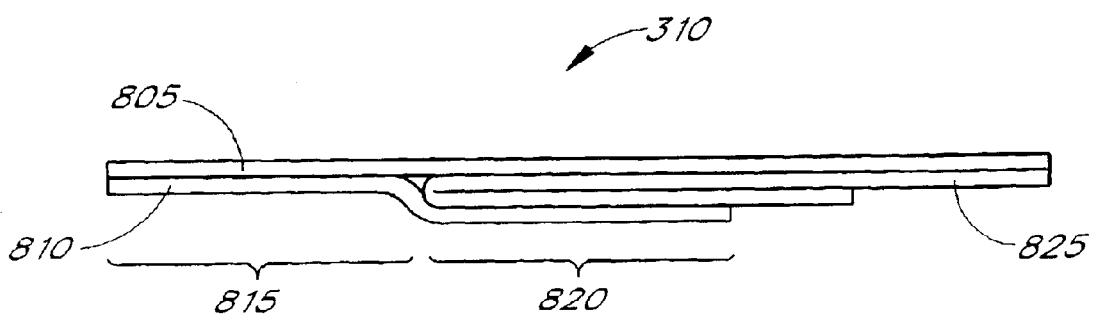

FIGS. 8A and 8B illustrate yet another embodiment of the disposable portion 310 of the resposable sensor 300. As shown in this embodiment, the disposable portion 310 includes a face tape layer 805 and a clear base tape layer 810. According to this embodiment, the clear base tape layer 810 includes a preattached section 815 and a fold over section 820. The preattached section 815 attaches approximately one third of the face tape layer 805 to the clear base tape layer 810. On the other hand, the fold over section 820 forms a flap configured to create a cavity between the face tape layer 805 and the clear base tape layer 810. The cavity is configured to receive the reusable portion 305 of the resposable sensor 300. According to one embodiment, a release liner 825 fills the cavity and separates the face tape layer 805 from the clear base tape layer 810. When the release liner 825 is removed, newly exposed adhesive on the fold over section 820 and the face tape layer 805 removably attaches the reusable portion 305 between the face tape layer 805 and fold over section 820 of the clear base tape layer 810.

According to another embodiment, the cavity is so formed that adhesive is not needed. For example, the fold over section 820 may comprise resilient material that can form a friction fit relationship so as to fix the reusable portion 305 in an appropriate position relative to the disposable portion 310. On the other hand, the fold over section 820 may also comprise material having other than resilient or adhesive properties, but still allow for proper placement of the reusable portion 305 and disposable portion 310 on the patient. For example, hook-and-loop type materials like VELCRO® may be used.

It will be understood that a skilled artisan would recognize that the fold over embodiment of the responsible sensor 300 may employ the properties discussed in relation to FIGS. 3–7, such as the information element 405 and the breakable wire 505.

Figure 9A:
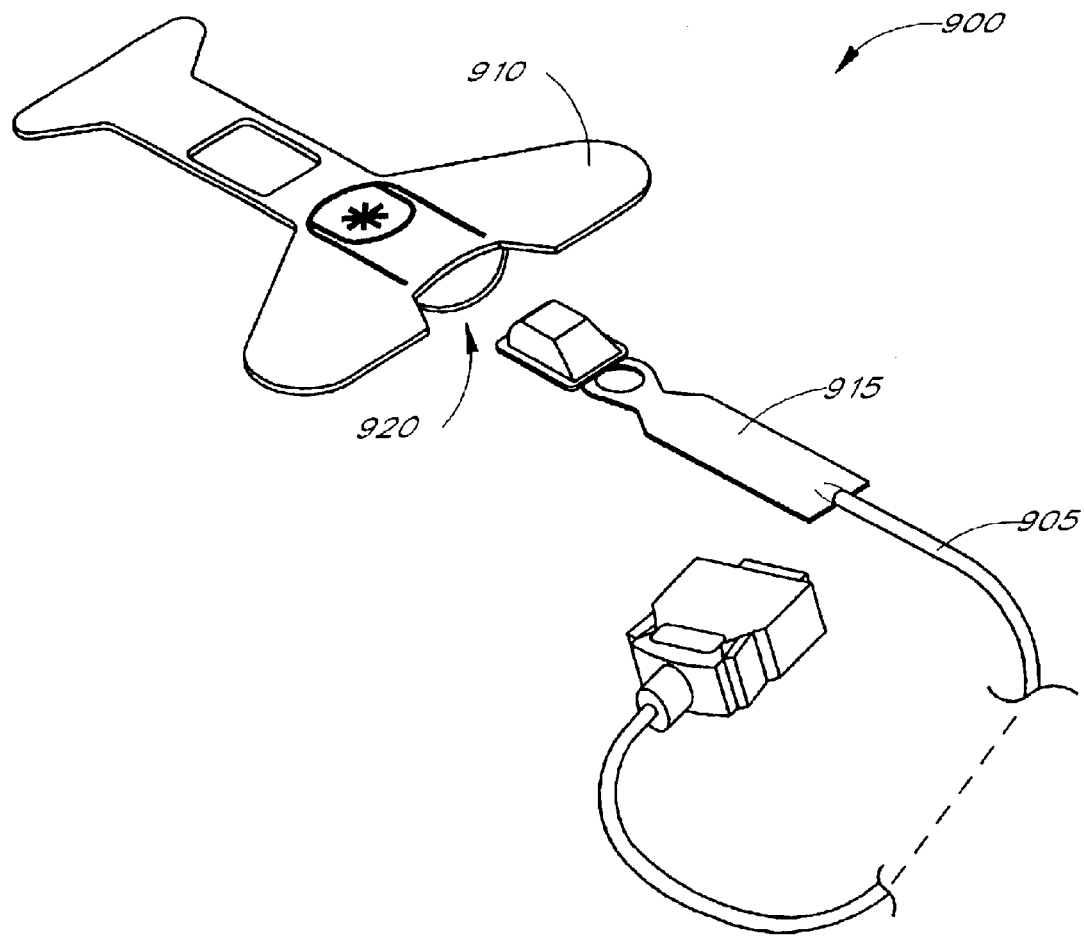
FIG. 9A illustrates a perspective view of a resposable sensor having a disposable portion configured as a tape sleeve and a reusable portion directly attached to a patient cable, according to another embodiment of the invention.

FIG. 9A illustrates an embodiment of a resposable sensor 900 integrated with an attached patient cable 905, according to another embodiment of the invention. In this embodiment, a disposable portion 910 is attached to a reusable portion 915 by removably inserting the reusable portion 915 into a tape envelope 920 formed in the disposable portion 910.

A skilled artisan will recognize that the disposable portion 910 may include the information element 405, the breakable wire 505, or both. Inclusion of one or both of these electronic components in the resposable sensor 900 advantageously provides the security, quality control, and safety features described in the foregoing embodiments.

FIG. 9B illustrates an embodiment of a resposable sensor 300 of FIG. 3, according to another embodiment of the invention. According to this embodiment, the resposable sensor 300 removably attaches to the patient cable 905 via a sensor connector 925. The patient cable 905 then attaches to an oximeter via an oximeter connector 930. Use of the sensor connector 925 enables the replacement of both the reusable portion 305 of the resposable sensor 300 without replacement of the sensor connector 925 or patient cable 905. In such an embodiment, the disposable portion 310 would follow a different, more frequent, replacement schedule than that of the reusable portion 305.

A skilled artisan will recognize that the variety of configurations described above that include the information element 405, the breakable wire 505, or both, may be incorporated into the embodiment of FIG. 9B.

Although the foregoing invention has been described in terms of certain preferred embodiments, other embodiments will be apparent to those of ordinary skill in the art. For example, select aspects of FIGS. 3–9B may be combined. For example, the envelope configured disposable portion 910 of FIG. 9A may be combined with the reusable portion 305 of FIG. 3. A resposable sensor is described in U.S. patent application Ser. No. 09/456,666 filed Dec. 9, 1999 entitled "Responsable Pulse Oximetry Sensor," assigned to Masimo Corporation, Irvine, Calif. and incorporated by reference herein.

Isolation And Communications Element

Figure 10:
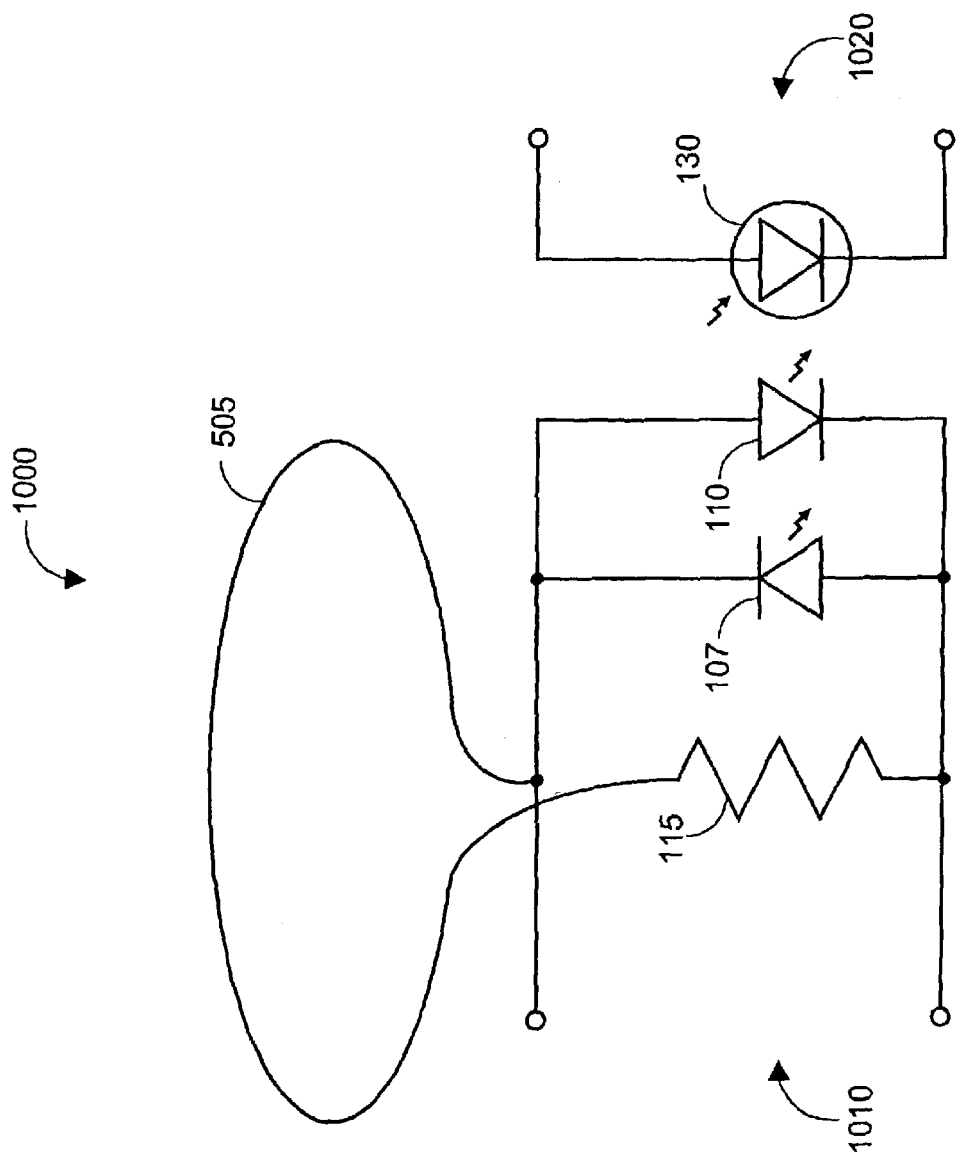
FIG. 10 is a schematic of a sensor circuit incorporating a breakable conductor.

FIG. 10 illustrates a sensor circuit 1000 incorporating a breakable conductor, as described above. The sensor circuit 1000 has emitters 107, 110, a corresponding detector 130, and an information element 115, as described with respect to FIG. 1. The sensor circuitry 1000 also has a breakable conductor 505, as described with respect to FIG. 5. Further, the sensor circuit 1000 has an emitter input 1010 and a detector output port 1020, which are both accessible via a connector 308 (FIG. 3). A pulse oximeter (not shown) attached to the connector 308 (FIG. 3) outputs emitter drive current to the emitter input 1010 and inputs a resulting detector current from the output port 1020, as described with respect to FIG. 1. The pulse oximeter also reads the information element 115 via the emitter input 1010, as described with respect to FIG. 1. Excessive wear results in a discontinuity in the breakable conductor 505, as described above. There are drawbacks, however, to this circuit configuration. If routed within the sensor face tape layer 315 (FIG. 5), as described with respect to FIGS. 5–7, the breakable conductor 505 reduces patient electrical isolation from the pulse oximeter. Further, the breakable conductor may act as an antenna for EMI and conduct the resulting electrical noise into the sensor circuitry.

Figure 11:
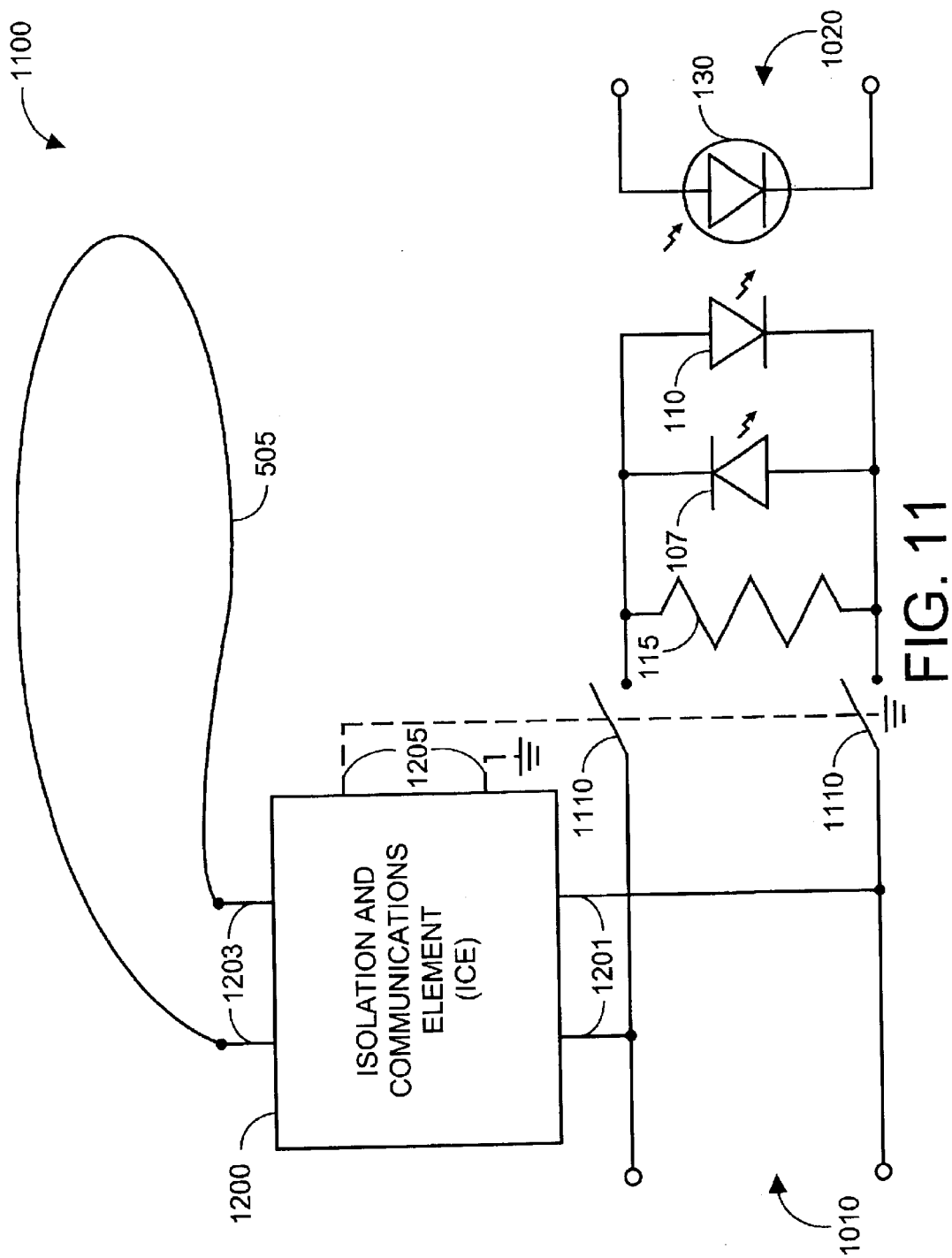
FIG. 11 is a schematic of a sensor circuit incorporating an embodiment of an isolation and communications element (ICE).

FIG. 11 illustrates a sensor circuit 1100 incorporating one embodiment of an isolation and communications element (ICE) 1200. In addition to the ICE 1200, the sensor circuit 1100 has a breakable conductor 505, an emitter input 1010, a detector output 1020, one or more switches 1110, emitters 107, 110, a detector 130 and an information element 115. The emitters 107, 110, detector 130 and information element 115 are described above. The ICE senses a discontinuity in the breakable conductor 505 and renders the sensor inoperable accordingly. The ICE is configured to optically isolate the breakable conductor 505 from the remainder of the sensor circuitry 1100 so as to improve electrical isolation of the patient from the pulse oximeter electrical supply and prevent electromagnetic interference (EMI) inductively coupled into the breakable conductor 505 from being conducted into the sensor circuitry 1100. Further, the ICE provides a communication feature, described below, that allows bi-directional data transfers between a pulse oximeter and the sensor, advantageously utilizing the emitter input 1010.

As shown in FIG. 11, this embodiment of the ICE 1200 is connected in parallel with the input 1010, and the switches 1110 are external to the ICE 1200. The ICE 1200 has a instrument port 1201, a loop port 1203 and a control port 1205. The instrument port 1201 connects in parallel to the emitter input 1010. The loop port 1203 provides a current loop that connects to the breakable conductor 505. The control port 1205 actuates the switches 1110, which connect the emitters 107, 110 to the emitter input 1010. The switches 1110 may be normally open or normally closed and actuated accordingly. Further, the switches may be electromechanical or purely electrical devices.

Also shown in FIG. 11, the instrument port 1201 taps current from the modulated signal which drives the emitters 107, 110, in order to supply power to the ICE 1200. The instrument port 1201 also provides bi-directional communications between the ICE 1200 and a pulse oximeter attached to the sensor connector 308 (FIG. 3). Advantageously, this bi-directional communications is conducted via the emitter input 1010, eliminating the need for additional connector pinouts. The loop port 1203 provides a current loop so as to detect discontinuities in the attached breakable conductor 505. In response to a breakable conductor discontinuity, the control port 1205 actuates one or more of the switches 1110 to an open position so as to disconnect the information element 115 or emitters 107, 110 from the emitter input 1010. In this manner, an attached pulse oximeter is unable to read the information element 115 and/or the sensor is otherwise rendered inoperable when the breakable conductor is broken.

Figure 12:
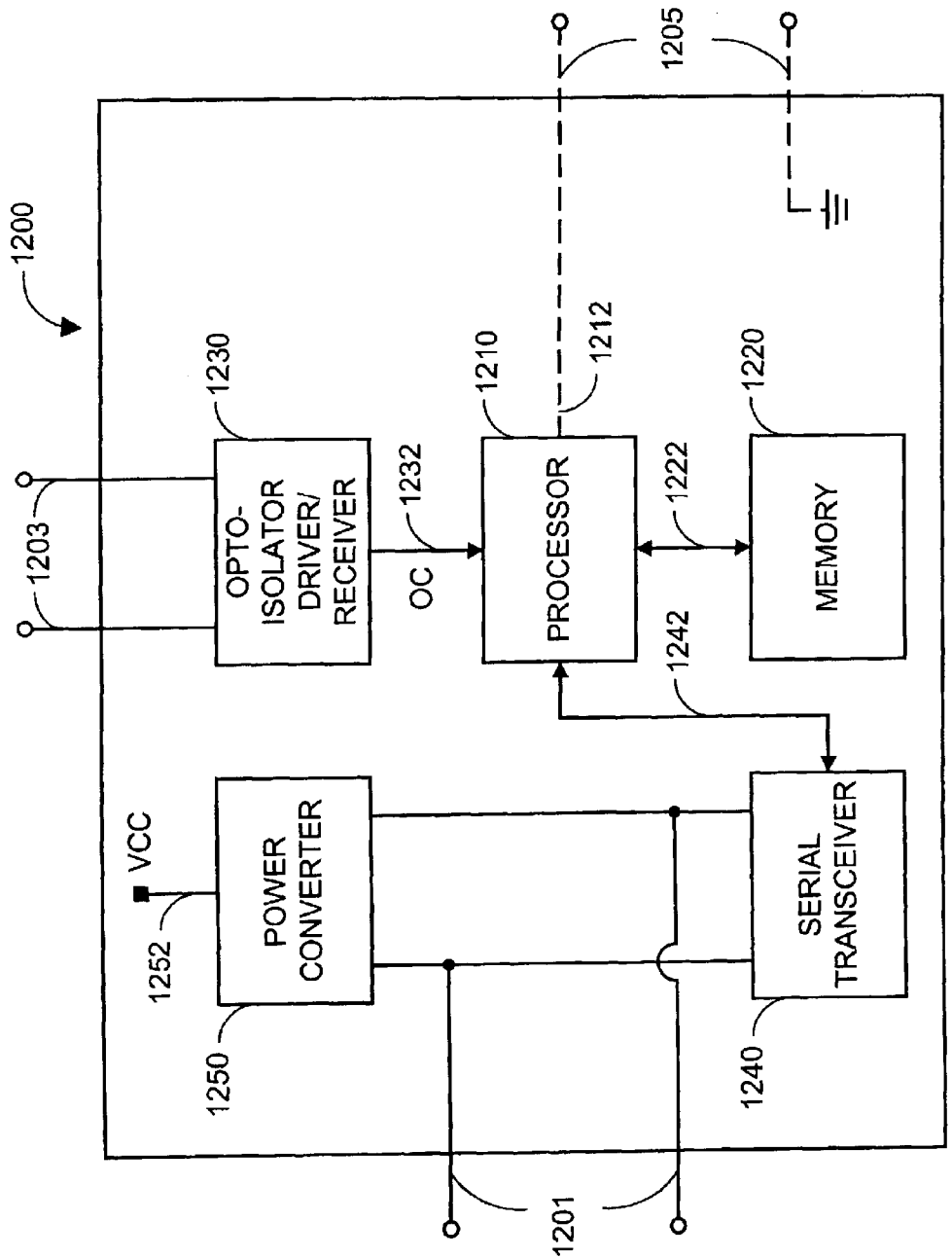
FIG. 12 is a block diagram of an ICE embodiment.

FIG. 12 illustrates one embodiment of an isolation and communications element 1200. The ICE 1200 has a processor 1210, a memory 1220, an opto-isolator driver/receiver 1230, a serial transceiver 1240, and a power converter 1250. The opto-isolator 1230 detects an open circuit at the loop port 1203 and asserts a logic output OC 1232 in response, indicating a discontinuity in the breakable conductor. The opto-isolator 1230 electrically isolates the loop port 1203 utilizing LED and photodiode pairs (not shown), as is well-known in the art. One pair drives the current loop created by the breakable conductor 505 (FIG. 11). Another pair detects an open-circuit, for example by measuring the voltage across a sampling resistor in series with the breakable conductor 505 (FIG. 11) and generating the OC logic output 1232 accordingly. The processor 1210 reads the OC output 1232 and, in response, generates a control output 1212 to the control port 1205, which actuates the switches 1110 (FIG. 11).

The power converter 1250 is an AC-to-DC converter that taps a portion of the modulated emitter drive current at the emitter input 1201 and provides one or more DC voltage outputs 1252 to power the remainder of the ICE 1200. The memory 1220 is connected to the processor 1210 with a bi-directional bus 1222 for transferring instructions and data. The memory 1220 may be volatile RAM or nonvolatile programmable ROM or a combination of RAM and PROM. The memory 1220 stores a variety of sensor information downloaded at the time of manufacture or during communications with a pulse oximeter, as described below.

As shown in FIG. 11, a modulated waveform applied to the emitter input 1201 for driving the emitters 107, 110 is described in U.S. Pat. No. 6,229,856 entitled "Method and Apparatus for Demodulating Signals in a Pulse Oximetry System" assigned to the assignee of the present application and incorporated by reference herein. In particular, a current is first applied in a forward direction with respect to one LED 107 during a first time interval. Thereafter, no current is applied to either LED 107, 110 during a second time interval. Then, current is applied in a forward direction with respect to the other LED 110 during a third time interval. Then, no current is applied to either LED 107, 110 during a fourth time interval. Thereafter, the current is again applied in the forward direction for one LED 107 during a fifth time interval that corresponds to the first time interval. Typically, each emitter 107, 110 is active for a duty cycle of 25%, and an inactive period having a 25% duty cycle separates each active period.

As shown in FIG. 12, the serial transceiver 1240 is connected to the emitter input 1201 and provides a bi-directional data bus 1242 to the processor 1210. During a start-up, calibration, initialization or re-initialization period, an attached instrument, such as a pulse oximeter or testing device, may alter the modulated waveform described above for the purpose of transmitting information to the sensor processor 1210. That is, the emitter drive current applied to the emitter input 1201 may be modulated in a manner other than a constant 25% on and 25% off cycle so as to convey information. For example, the current waveform may be pulse position modulated (PPM) or pulse width modulated (PWM) with a bit pattern, as is well known in the art. Transmitted bit patterns may contain information such as calibration data, emitter specifications, and/or manufacturing data to name a few. The serial transceiver 1240 demodulates this data, which is then transferred over the data bus 1242 to the processor 1210, either as serial or parallel data. The processor 1210 may in turn store this information in memory 1220.

Further, the serial transceiver 1240 may also transfer data from the processor 1210 to an attached instrument. A data upload may occur during emitter "off" periods, described above, which may be the 25% duty off-cycles or specifically designated off periods timed so that the power converter 1250 is still operational. The upload may be at a voltage that is less than the turn-on voltage of either emitter 107, 110 so as to limit the required output power from the ICE 1200. Alternatively, the emitters may be disconnected during data uploads by the switches 1110 (FIG. 11). The data upload may be accomplished by any of a number of conventional serial data transfer waveforms, such as PPM or PWM to name a few.

Figure 13:
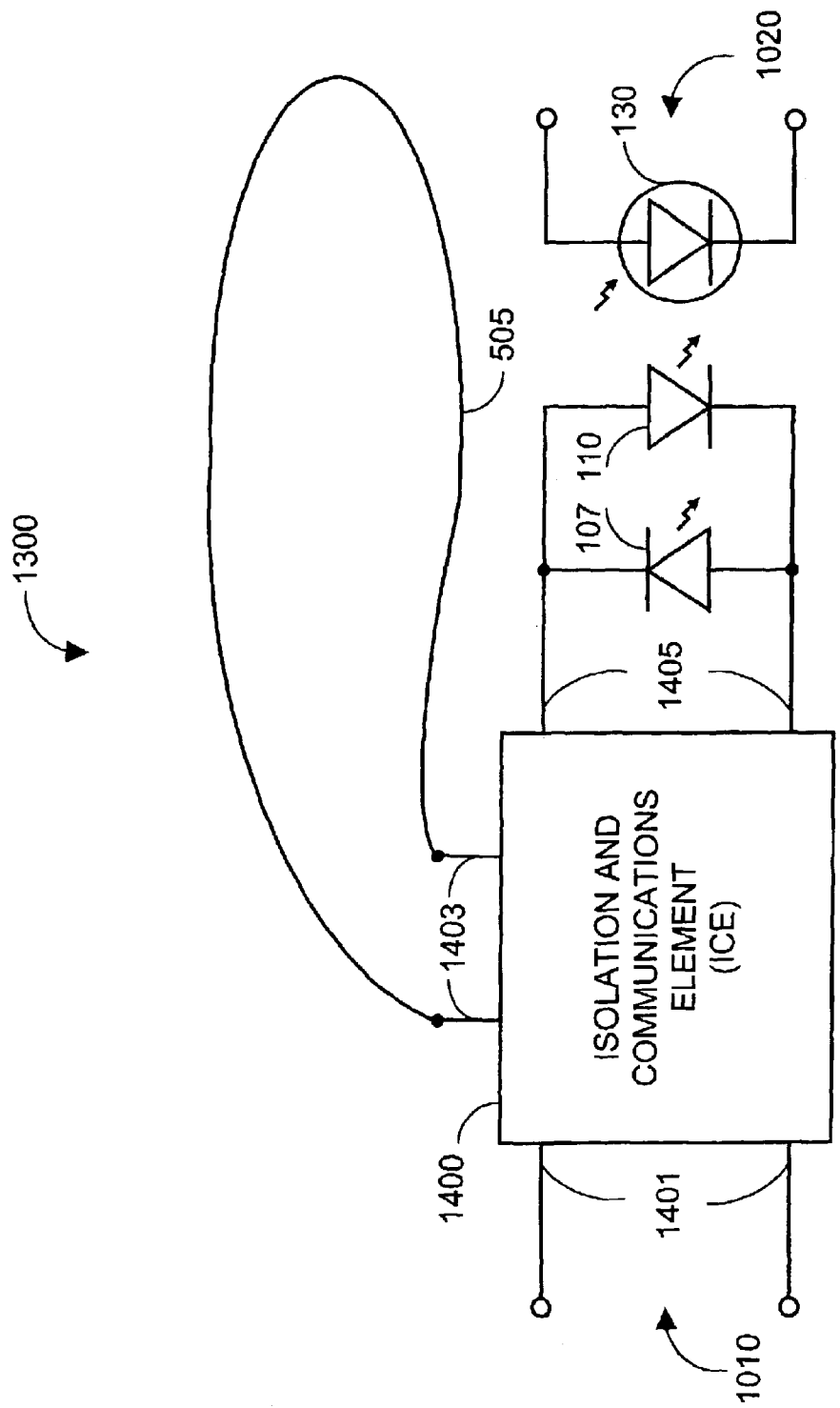
FIG. 13 is a schematic of a sensor circuit incorporating an alternative embodiment of an isolation and communications element (ICE).
Figure 14:
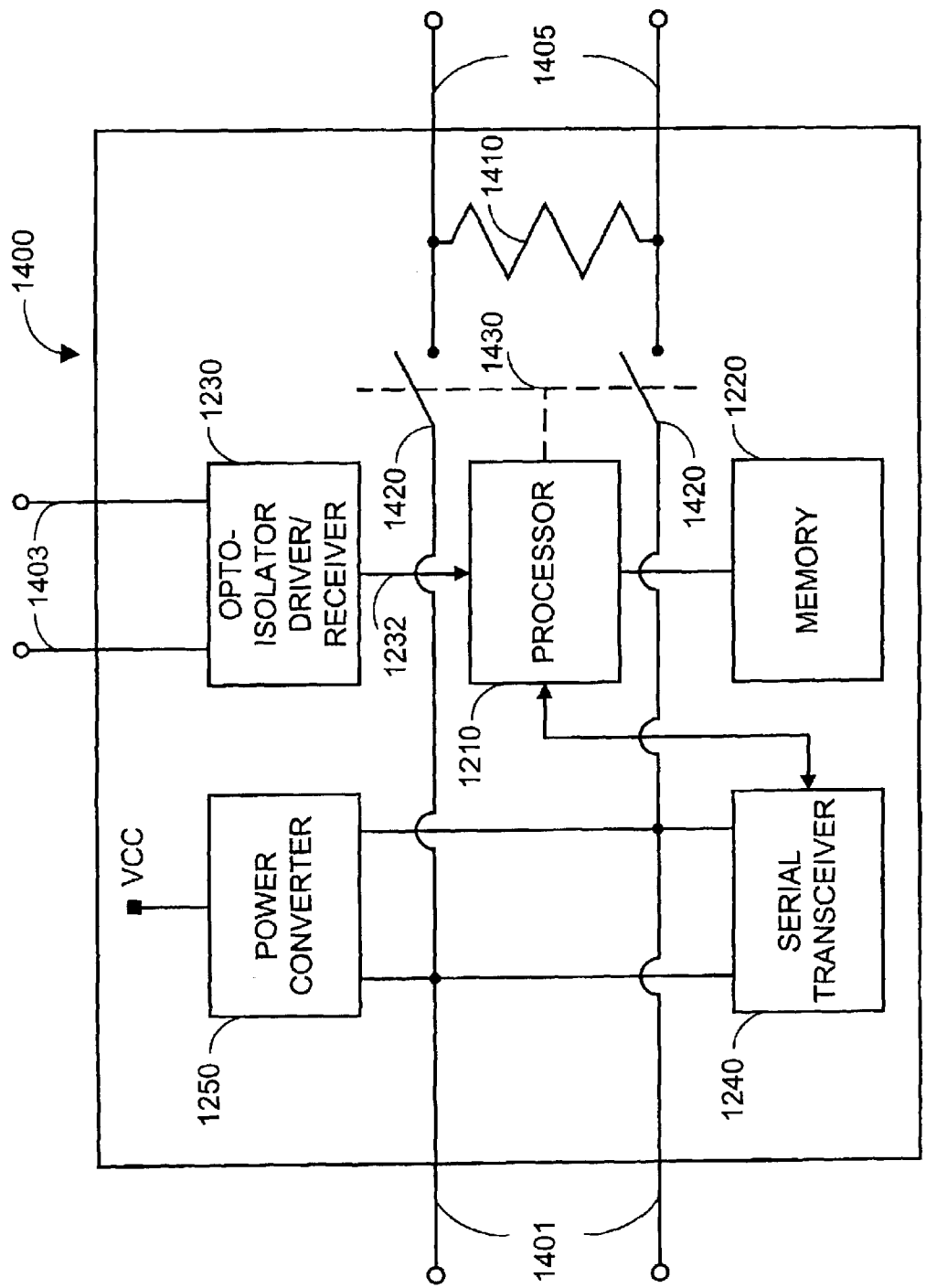
FIG. 14 is a block diagram of an alternative ICE embodiment.

FIG. 13 illustrates a sensor circuit 1300 incorporating an alternative embodiment of an isolation and communications element 1400. The sensor circuit 1300 has a breakable conductor 505, an emitter input 1010, a detector output port 1020, emitters 107, 110 and a detector 130 as described with respect to FIG. 11, above. In this embodiment, the ICE 1400 is connected in series between the emitter input 1010 and the emitters 107, 110 and utilizes internal switches 1420 (FIG. 14). The ICE 1400 has a instrument port 1401 and a loop port 1403, also as described with respect to FIG. 11, above. Further, the ICE 1400 has a component port 1405 that connects to the emitters 107, 110. The ICE 1400 decouples the breakable conductor 505 from the emitter input 1010 and other portions of the sensor circuit 1300, such as the detector 130, as described with respect to FIG. 11, above. The instrument port 1401 taps power from the modulated drive signal on the emitter input 1010 and provides bi-directional communications between the ICE 1400 and an attached pulse oximeter, also as described with respect to FIG. 11, above.

FIG. 14 illustrates a block diagram of an alternative embodiment of an isolation and communications element 1400. The ICE 1400 has a processor 1210, a memory 1220, an opto-isolator driver/receiver 1230, a serial transceiver 1240, and a power converter 1250, as described with respect to FIG. 12, above. The ICE also has an internal information element 1410 and one or more internal switches 1420. In response to a breakable conductor discontinuity as signaled by the OC logic output 1232 of the opto-isolator 1230, the processor 1210 generates a control output 1430 that activates the switches 1420. When activated, the switches 1420 disconnect the component port 1405 from the emitter input 1010. In this manner, the information element 1410 cannot be read by an attached pulse oximeter and/or the sensor is rendered otherwise inoperable when the breakable conductor is broken Other combinations, omissions, substitutions and modifications of the ICE embodiments and the ICE-sensor circuit configurations will be apparent to the skilled artisan in view of the disclosure herein. For example, the sensor circuit was described as having back-to-back emitters and a parallel connected information element all sharing a pair of connector pinouts. The ICE, however, can also be configured with a sensor circuit having emitters and an information element with only partially shared pinouts, such as common cathode or common anode configurations, or with unshared pinouts. As another example, the sensor circuit was described with switches actuated to disconnect sensor components from the sensor connector. Other devices that can be actuated to decouple one or more sensor components from the sensor connector may be used, such as high impedance capable series devices or low impedance capable parallel devices. Further, the isolation and communications element (ICE) is described in the conjunctive, it is understood that a sensor may be configured with either an isolation function or a communications element or both.

What is claimed is:

1. A sensor comprising:
   a connector adapted to electrically communicate with a physiological measurement instrument;
   a breakable conductor that transitions from a continuity state to a discontinuity state as the result of sensor wear; and
   an isolation and communications element (ICE) having an instrument port and an electrically isolated loop port, said instrument port in communications with said connector and said loop port in communications with said breakable conductor, wherein:
   said ICE further comprises a control output responsive to said discontinuity state, said sensor further comprises an electrical component, said ICE being connected in parallel with said connector and said electrical component, and said component being operable from said instrument via said connector according to said control output.

2. The sensor according to claim 1 further comprising a switch in series between said component and said connector, said switch responsive to said control output so as to disconnect said component from said connector.

3. The sensor according to claim 2 wherein said ICE further comprises a converter which supplies DC power to said ICE, said converter connected to said instrument port so as to draw modulated power from said instrument.

4. The sensor according to claim 2 wherein said ICE further comprises:
   a processor having an input indicating said discontinuity state and providing said control output in response;
   a transceiver in communications with said processor and said instrument port and adapted to transfer a plurality of data items between said instrument and said processor; and
   a memory readable and writeable by said processor and adapted to store and retrieve said data items.

5. The sensor according to claim 2 wherein said ICE further comprises:
   an opto-isolator driver connected to said loop port and adapted to supply a current to said breakable conductor; and
   an opto-isolator receiver connected to said loop port and adapted to receive said current so as to detect said discontinuity state.

6. A sensor comprising:
   a connector adapted to electrically communicate with a physiological measurement instrument;
   a breakable conductor configured as a current loop that becomes an open circuit as the result of sensor wear, said conductor electrically isolated from said connector;
   an electrical component operable from said instrument via said connector said electrical component rendered inoperable in response to said open circuit;
   a driver configured to provide a current to said breakable conductor; and
   a receiver responsive to said current so as to provide a control output indicating said open circuit, wherein said driver and said receiver are adapted to provide electrical isolation between said conductor and said connector.

7. The sensor according to claim 6 further comprising a switch between said component and said connector, said switch actuated by said control output so as to disconnect said component from said connector.

8. The sensor according to claim 7 wherein said component is an information element readable by said instrument so as to activate said sensor, said switch rendering said information element unreadable when said control output indicates said open circuit.

9. A sensor method comprising the steps of: incorporating a breakable conductor within a sensor to indicate sensor wear;
   isolating said conductor from a measurement connector; and
   disabling a sensor circuit in response to a discontinuity in said breakable conductor, wherein said isolating step comprises the substeps of:
   providing a current for said conductor from an optically isolated driver; and
   detecting said current in said conductor by an optically isolated receiver.

10. The sensor method according to claim 9 wherein said disabling step comprises the substeps of:
    generating an open circuit output from said receiver when said current is disrupted; and
    actuating a switch in response to said open circuit output to disconnect said sensor circuit from said connector.

11. The sensor method according to claim 10 comprising the further steps of:
    detecting a communications request at said measurement connector;
    actuating said switch in response to said communications request; and
    downloading data from said connector to a sensor memory.

12. A sensor configured to connect to a measurement instrument comprising:
    a conductive means for indicating sensor wear;
    an optical means for isolating said conductive means from said instrument; and
    a switching means for disabling a circuit portion of said sensor in response to a discontinuity in said conductive means.

13. The sensor according to claim 12 further comprising a communications means for the transfer of data between said instrument and said sensor.

14. The sensor according to claim 12 further comprising a converter means for drawing power from said instrument and supplying power to said sensor.

* * * * *

UNITED STATES PATENT AND TRADEMARK OFFICE
CERTIFICATE OF CORRECTION

PATENT NO.        : 6,950,687 B2
APPLICATION NO. : 10/351643
DATED             : September 27, 2005
INVENTOR(S)       : Al-Ali It is certified that error appears in the above-identified patent and that said Letters Patent is hereby corrected as shown below:

Title Page, item [73] (Assignee), line 1, delete "Irvine, CA" and insert -- 41 Parker Irvine, CA 92618 --, therefore.

First Page, column 2 (Other Publications), line 16, delete "Sensors,," and insert -- sensors, --, therefore.

At column 2, line 39, delete "electromagnetic" and insert -- electro-magnetic --, therefore.

At column 9, line 3, delete "a" and insert -- an --, therefore.

At column 10, line 45, delete "a" and insert -- an --, therefore.

At column 11, line 4, after "broken" insert -- . --.

Signed and Sealed this

Nineteenth Day of June, 2007

JON W. DUDAS
*Director of the United States Patent and Trademark Office*